(12) United States Patent
Sapir (10) Patent No.: US 9,668,674 B2
(45) Date of Patent: Jun. 6, 2017

(54) MEASUREMENT OF APPENDAGE OPENINGS

(71) Applicant: TRANSSEPTAL SOLUTIONS LTD., Kefar Monash (IL)

(72) Inventor: Elad Sapir, Kefar Yona (IL)

(73) Assignee: TRANSSEPTAL SOLUTIONS LTD., Kefar Monash (IL)

( * ) Notice: Subject to any disclaimer, the term of this patent is extended or adjusted under 35 U.S.C. 154(b) by 76 days.

(21) Appl. No.: 14/636,759

(22) Filed: Mar. 3, 2015

(65) Prior Publication Data

US 2016/0256075 A1 Sep. 8, 2016

(51) Int. Cl.
*A61B 5/00* (2006.01)
*A61B 5/107* (2006.01)
*A61B 5/02* (2006.01)
*A61F 2/24* (2006.01)
*A61B 90/00* (2016.01)

(52) U.S. Cl.
CPC .......... *A61B 5/1076* (2013.01); *A61B 5/0044* (2013.01); *A61B 5/02028* (2013.01); *A61B 5/1079* (2013.01); *A61B 5/6856* (2013.01); *A61B 2090/061* (2016.02); *A61B 2090/3966* (2016.02); *A61B 2576/023* (2013.01); *A61F 2/2496* (2013.01)

(58) Field of Classification Search
CPC ....... A61B 5/11; A61B 5/1127; A61B 5/1128; A61B 5/107; A61B 5/1076; A61B 5/6856; A61B 5/02086; A61B 5/1079; A61B 5/0044; A61B 19/46; A61B 2019/464–2019/466; A61B 2090/061; A61B 2090/3966; A61B 2576/023; A61F 2/243; A61F 2/2445; A61F 2/2472; A61F 2/2496
USPC ........................................................ 600/587
See application file for complete search history.

(56) References Cited

U.S. PATENT DOCUMENTS

| | | | | |
|---|---|---|---|---|
| 5,010,892 A | * | 4/1991 | Colvin | A61B 5/1076 600/587 |
| 5,042,161 A | * | 8/1991 | Hodge | A61B 5/1076 33/501.45 |
| 5,489,296 A | * | 2/1996 | Love | A61F 2/2496 600/587 |
| 5,497,774 A | | 3/1996 | Swartz | |

(Continued)

FOREIGN PATENT DOCUMENTS

| | | |
|---|---|---|
| DE | 102005023414 | 11/2006 |
| EP | 0808607 | 11/1997 |

(Continued)

OTHER PUBLICATIONS

An International Search Report and Written Opinion issued in PCT/IL2015/051026, dated Mar. 30, 2016.

(Continued)

*Primary Examiner* — Max Hindenburg
(74) *Attorney, Agent, or Firm* — Sughrue Mion, PLLC (57) ABSTRACT

Apparatus and methods are described, including a method for measuring an opening of an appendage of an atrium of a subject. A catheter is inserted into the atrium, and at least one loop is deployed from a wall of the catheter, such that a distal end of the loop is distal to a distal end of the catheter. The loop is used to measure the opening of the appendage. Other applications are also described.

17 Claims, 9 Drawing Sheets

(56) References Cited

U.S. PATENT DOCUMENTS

| | | | |
|---|---|---|---|
| 5,507,743 A | 4/1996 | Edwards | |
| 5,605,543 A | 2/1997 | Swanson | |
| 5,807,395 A | 9/1998 | Mulier | |
| 5,885,228 A * | 3/1999 | Rosenman | A61F 2/2496 600/587 |
| 5,910,150 A | 6/1999 | Saadat | |
| 6,033,359 A * | 3/2000 | Doi | A61B 5/1076 600/104 |
| 6,102,926 A | 8/2000 | Tartaglia | |
| 6,575,921 B2 * | 6/2003 | Vanden Hoek | A61B 5/107 33/511 |
| 6,623,448 B2 | 9/2003 | Slater | |
| 6,623,449 B2 | 9/2003 | Paskar | |
| 6,629,534 B1 | 10/2003 | St. Goar et al. | |
| 6,641,564 B1 | 11/2003 | Kraus | |
| 6,650,923 B1 | 11/2003 | Lesh | |
| 6,796,963 B2 | 9/2004 | Carpenter et al. | |
| 7,048,733 B2 | 5/2006 | Hartley | |
| 7,344,543 B2 | 3/2008 | Sra | |
| 7,581,328 B2 | 9/2009 | Greenhalgh et al. | |
| 7,615,014 B2 * | 11/2009 | Omata | A61B 5/103 600/587 |
| 7,635,353 B2 | 12/2009 | Gurusamy | |
| 7,641,638 B2 | 1/2010 | Waxman et al. | |
| 7,654,970 B2 * | 2/2010 | Dubey | A61B 5/036 600/488 |
| 7,666,203 B2 | 2/2010 | Chanduszko | |
| 7,815,577 B2 | 10/2010 | Krishnan | |
| 7,824,341 B2 | 11/2010 | Krishnan | |
| 7,850,644 B2 | 12/2010 | Gonzalez | |
| 7,976,551 B1 | 7/2011 | Gutfinger | |
| 8,000,809 B2 | 8/2011 | Elencwajg | |
| 8,012,106 B2 * | 9/2011 | Mangiardi | A61B 5/1076 600/484 |
| 8,019,404 B2 | 9/2011 | Kapadia | |
| 8,029,470 B2 | 10/2011 | Whiting | |
| 8,114,110 B2 | 2/2012 | Bednarek | |
| 8,172,757 B2 | 5/2012 | Jaffe | |
| 8,235,986 B2 | 8/2012 | Kulesa | |
| 8,251,963 B2 | 8/2012 | Chin et al. | |
| 8,292,910 B2 | 10/2012 | Chanduszko et al. | |
| 8,317,810 B2 | 11/2012 | Stangenes | |
| 8,663,168 B2 | 3/2014 | Chin et al. | |
| 8,694,077 B2 | 4/2014 | Kapadia | |
| 8,771,297 B2 | 7/2014 | Millet et al. | |
| 8,911,384 B2 * | 12/2014 | Santiago | A61B 5/1072 33/512 |
| 9,005,139 B2 * | 4/2015 | Klaiman | A61B 5/02007 600/587 |
| 9,339,230 B2 * | 5/2016 | Kassab | A61B 5/053 |
| 9,345,574 B2 * | 5/2016 | Conklin | A61F 2/2496 |
| 2002/0026175 A1 | 2/2002 | Paskar | |
| 2002/0038129 A1 | 3/2002 | Peters | |
| 2002/0143291 A1 | 10/2002 | Slater | |
| 2002/0169377 A1 | 11/2002 | Khairkhahan | |
| 2003/0125709 A1 | 7/2003 | Eidenschink | |
| 2003/0144657 A1 | 7/2003 | Bowe | |
| 2004/0220471 A1 | 11/2004 | Schwartz | |
| 2004/0225304 A1 | 11/2004 | Vidlund et al. | |
| 2005/0101984 A1 | 5/2005 | Chanduszko | |
| 2005/0149097 A1 | 7/2005 | Regnell | |
| 2006/0064062 A1 | 3/2006 | Gurusamy | |
| 2006/0074398 A1 | 4/2006 | Whiting | |
| 2006/0276710 A1 | 12/2006 | Krishnan | |
| 2007/0270741 A1 | 11/2007 | Hassett | |
| 2008/0097398 A1 | 4/2008 | Mitelberg | |
| 2008/0161840 A1 | 7/2008 | Osiroff | |
| 2009/0171276 A1 | 7/2009 | Bednarek | |
| 2009/0312755 A1 | 12/2009 | Thapliyal et al. | |
| 2010/0022948 A1 | 1/2010 | Wilson | |
| 2010/0168777 A1 | 7/2010 | Stangenes | |
| 2011/0054487 A1 | 3/2011 | Farnan | |
| 2011/0082538 A1 | 4/2011 | Dahlgren et al. | |
| 2011/0251594 A1 | 10/2011 | Godin | |
| 2011/0270239 A1 | 11/2011 | Werneth | |
| 2011/0295107 A1 | 12/2011 | Kargar et al. | |
| 2011/0313283 A1 | 12/2011 | Kapadia | |
| 2012/0022427 A1 | 1/2012 | Kapadia | |
| 2012/0065597 A1 | 3/2012 | Cohen | |
| 2012/0179188 A1 | 7/2012 | Chanduszko | |
| 2013/0123620 A1 | 5/2013 | Tekulve | |
| 2013/0274784 A1 | 10/2013 | Lenker | |
| 2014/0081302 A1 | 3/2014 | Thapliyal et al. | |
| 2014/0309675 A1 | 10/2014 | Maisano et al. | |
| 2014/0309678 A1 | 10/2014 | Maisano et al. | |
| 2014/0309679 A1 | 10/2014 | Maisano et al. | |
| 2016/0100859 A1 | 4/2016 | Sapir | |

FOREIGN PATENT DOCUMENTS

| | | |
|---|---|---|
| WO | 2011/130456 | 10/2011 |
| WO | 2013/128461 | 9/2013 |
| WO | 2014/064694 | 5/2014 |
| WO | 2014/170890 | 10/2014 |
| WO | 2016/059638 | 4/2016 |

OTHER PUBLICATIONS

A non-final office action issued in U.S. Appl. No. 14/287,523, dated Jul. 21, 2016.

A non-final office action issued in U.S. Appl. No. 14/513,435, dated Aug. 23, 2016.

An International Search Report and a Written Opinion both dated Sep. 30, 2014, which issued during the prosecution of Applicant's PCT/IL2014/050338.

U.S. Appl. No. 61/811,947, filed Apr. 15, 2013.

An Office Action dated Sep. 9, 2015, which issued during the prosecution of U.S. Appl. No. 14/245,135.

An Office Action dated Jan. 21, 2016, which issued during the prosecution of U.S. Appl. No. 14/287,523.

An Office Action dated Jan. 22, 2016, which issued during the prosecution of U.S. Appl. No. 14/287,470.

U.S. Appl. No. 62/095,150, filed Dec. 22, 2014.

An International Preliminary Report on Patentability dated Oct. 20, 2015, which issued during the prosecution of Applicant's PCT/IL2014/050338.

An Invitation to pay additional fees dated Jan. 15, 2016, which issued during the prosecution of Applicant's PCT/IL2015/051026.

An Office Action dated Feb. 9, 2016, which issued during the prosecution of U.S. Appl. No. 14/245,135.

\* cited by examiner

MEASUREMENT OF APPENDAGE OPENINGS

FIELD OF THE INVENTION

Applications of the present invention relate to finding and/or measuring openings inside a human body, such as an opening of a left atrial appendage (LAA).

BACKGROUND

In some cases, a subject may require an implant to close off his left atrial appendage.

SUMMARY OF THE INVENTION

Applications of the present invention include a method for measuring an opening of an appendage of an atrium (e.g., an LAA) of a subject, e.g., for purposes of implanting an implant at the opening. A catheter is inserted into the atrium, and at least one loop is deployed from a wall of the catheter, such that the distal end of the loop is distal to the distal end of the catheter. The loop is used to measure the opening of the appendage.

There is therefore provided, in accordance with some applications of the present invention, a method for measuring an opening of an appendage of an atrium of a subject, the method including:

inserting a catheter into the atrium of the subject;

deploying at least one loop from a wall of the catheter, such that a distal end of the loop is distal to a distal end of the catheter; and using the loop to measure the opening of the appendage.

In some applications, deploying the loop from the wall of the catheter includes deploying the loop from a lateral wall of the catheter.

In some applications, the method includes measuring an opening of an appendage of a left atrium of the subject.

In some applications, deploying the loop includes deploying the loop such that a normal to a plane defined by the loop intersects a line that is parallel to a longitudinal axis of the catheter at an angle that is between 10 and 90 degrees.

In some applications, the method further includes, before measuring the opening:

moving the distal end of the loop along a wall of the atrium; and identifying the opening in response to the distal end of the loop reaching the opening.

In some applications, the method further includes:

in response to the measuring, selecting an implant of an appropriate size;

delivering the implant to the opening, by passing the implant through the catheter; and implanting the implant in the opening.

In some applications, measuring the opening includes:

expanding the loop until the loop contacts at least two points on a perimeter of the opening; and measuring a distance between the points, by using imaging to view the loop while it is in contact with the points.

In some applications, measuring the opening includes:

expanding the loop until the loop contacts at least two points on a perimeter of the opening; and measuring a distance between the points, by utilizing a marker on a proximal portion of the loop that indicates an extent to which the loop has been expanded.

In some applications, the atrium is a left atrium, the loop is an appendage-finding loop, and the method further includes, prior to inserting the catheter into the left atrium:

inserting the catheter into a right atrium of the subject;

deploying at least one fossa-ovalis-finding loop from the wall of the catheter;

moving the fossa-ovalis-finding loop along an interatrial septum of the subject, until the fossa-ovalis-finding loop contacts a fossa ovalis of the subject; and in response to the fossa-ovalis-finding loop contacting the fossa ovalis, puncturing the fossa ovalis by passing a puncturing element out of the distal end of the catheter.

In some applications, the fossa-ovalis-finding loop is the appendage-finding loop.

In some applications, the fossa-ovalis-finding loop is different from the appendage-finding loop.

In some applications, the loop includes a longitudinal member that passes through a first opening and a second opening in the catheter wall, and deploying the loop includes deploying the loop by passing the longitudinal member through at least one of the first and second openings.

In some applications, deploying the at least one loop includes deploying at least two loops.

In some applications, deploying the at least two loops includes deploying more than two loops.

In some applications, measuring the opening of the appendage includes measuring (a) a distance between a first pair of points on a perimeter of the opening, and (b) a distance between a second pair of points on the perimeter of the opening.

The present invention will be more fully understood from the following detailed description of applications thereof, taken together with the drawings, in which:

DETAILED DESCRIPTION OF APPLICATIONS

Reference is made to FIGS. 1A-D, which are schematic illustrations of apparatus 34 for puncturing a fossa ovalis 18 of a subject, in accordance with some applications of the present invention. Apparatus 34 comprises a catheter 38, which may also be referred to by those in the field as an introducer tube. Catheter 38 is shaped to define a catheter lumen 52.

Figure 1A:
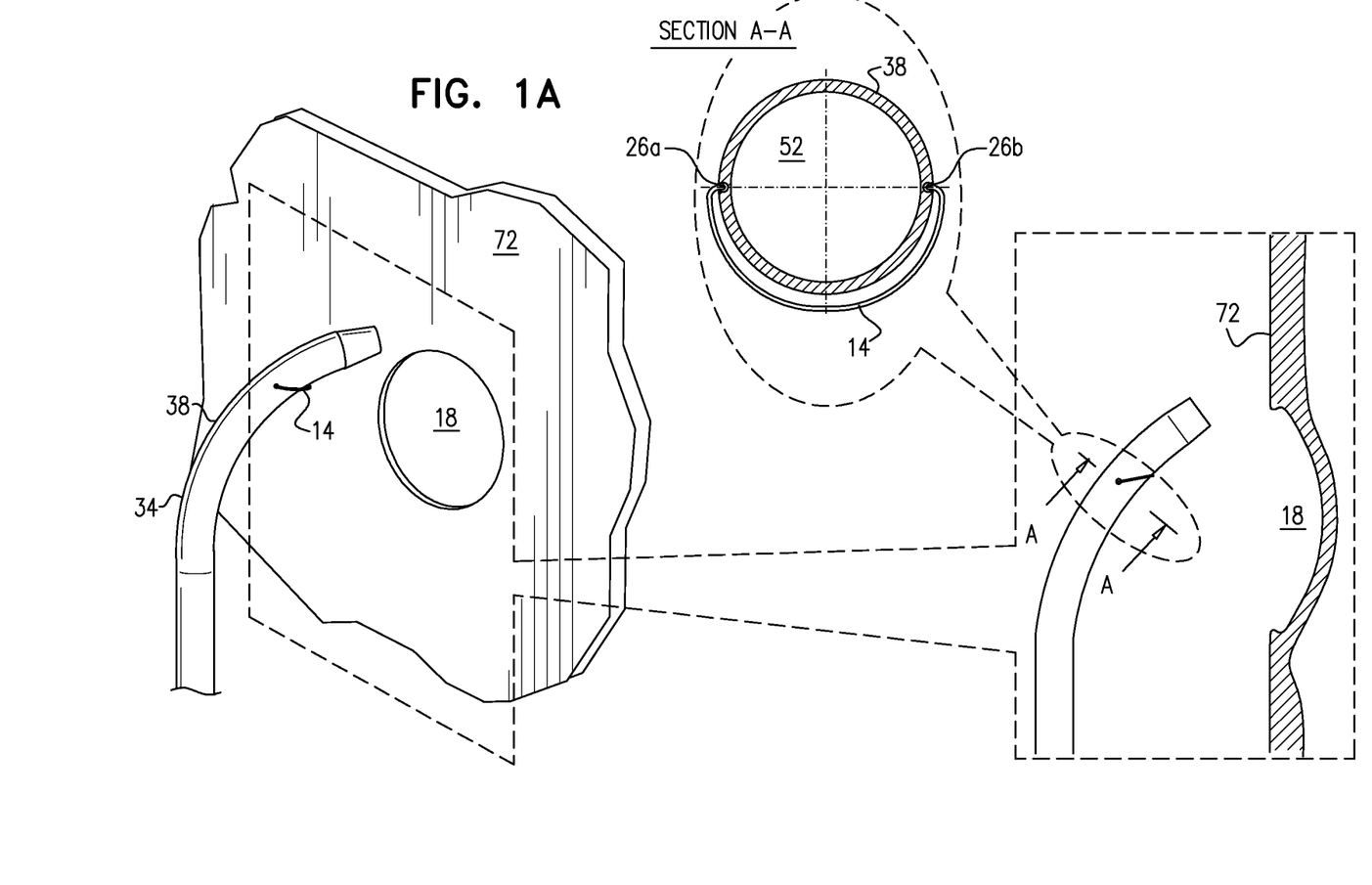
FIGS. 1A-1D are schematic illustrations of apparatus for puncturing a fossa ovalis of a subject, in accordance with some applications of the present invention.
Figure 2A:
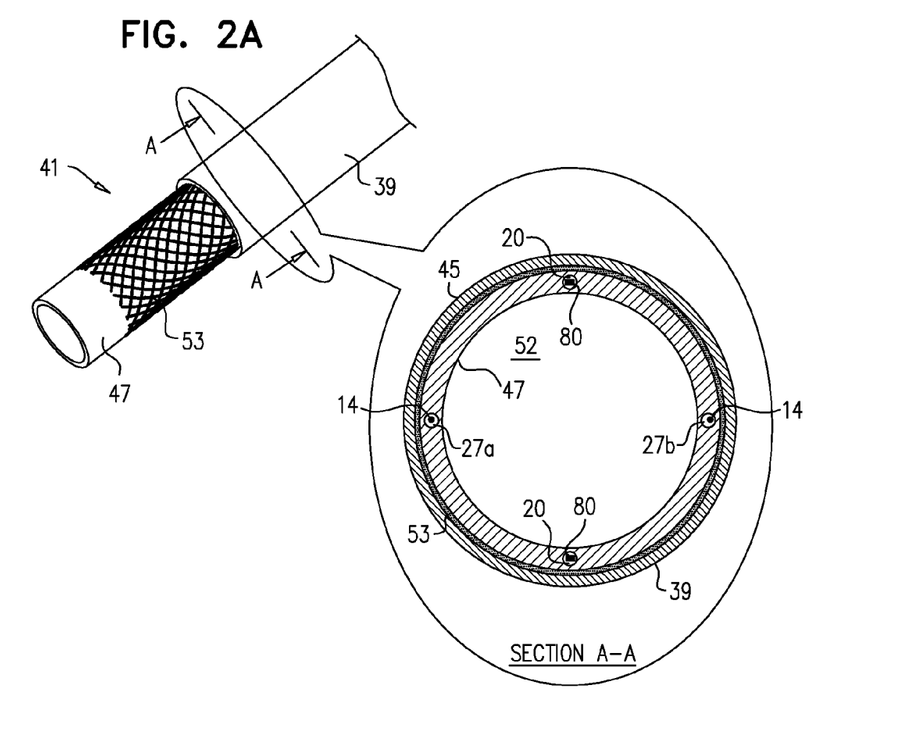
FIGS. 2A-2B are schematic illustrations of a cross-section of a wall of a catheter, in accordance with some applications of the present invention.
Figure 2B:
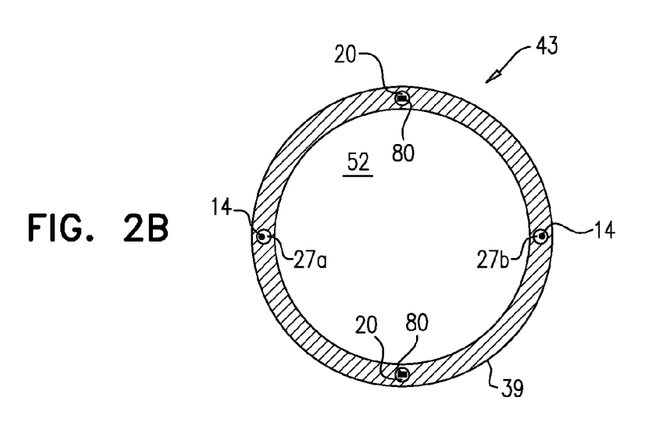

Reference is also made to FIGS. 2A-B, which are schematic illustrations of a cross-section of a wall 39 of catheter 38, in accordance with some applications of the present invention. Wall 39 comprises a braided portion 41 (FIG. 2A), which has an outer surface 45, an inner surface 47, and a braided interior 53 between outer surface 45 and inner surface 47. Wall 39 also comprises an unbraided portion 43 (shown in cross-section in FIG. 2B), which is typically disposed proximally to braided portion 41. Wall 39 is shaped to define a first longitudinally-running channel 27a and a second longitudinally-running channel 27b therethrough. (Channels 27a and 27b run through both the braided and unbraided portions.) A distal portion of catheter 38 is shaped to define a first lateral opening 26a and a second lateral opening 26b (FIG. 1A). A flexible longitudinal member 14 (e.g., a wire) passes (a) from a proximal portion of the catheter to the distal portion of the catheter via first channel 27a, (b) out of the first channel via first lateral opening 26a, (b) into second channel 27b via second lateral opening 26b, and (c) from the distal portion of the catheter to the proximal portion of the catheter via the second channel.

Typically, flexible longitudinal member 14 is mechanically resilient, i.e., it does not readily buckle upon being subjected to a compressive force, as would, for example, a string. The flexible longitudinal member typically comprises nitinol, stainless steel, and/or chromium cobalt, and typically has a diameter D that is at least 0.1 mm and/or less than 0.5 mm.

Catheter 38 is typically inserted into a vein in the pelvic area of the subject (e.g., the femoral vein), advanced toward the heart through the inferior vena cava, and inserted into the right atrium of the subject's heart. (Typically, catheter 38 is contained within the lumen of a sheath during parts of the insertion and/or withdrawal of the catheter, such as to reduce the risk of damage to surrounding tissue.) Following the insertion into the right atrium, the distal portion of catheter 38 is advanced toward interatrial septum 72 of the heart (FIG. 1A). Subsequently, as shown in FIG. 1B, the following two steps are performed sequentially (in either order), or simultaneously:

(a) A needle 32 is inserted into catheter lumen 52. Needle 32 is shaped to be slidably disposed within the catheter lumen. Typically, a dilator element 49 shaped to define a dilator lumen is shaped to be slidably disposed within the catheter lumen, and the needle is shaped to be slidably disposed within the dilator lumen. The needle is inserted into the dilator lumen, and is advanced up to tip 16 of the dilator element. (Although dilator element 49 may also be embodied as a catheter, the present description refers exclusively to catheter 38—the "introducer tube"—as a catheter.)

(b) Flexible longitudinal member 14 is deployed from the catheter, such that (i) a deployed portion of the flexible longitudinal member is loop-shaped, and (ii) the needle is on a first side of the deployed portion of the flexible longitudinal member. Typically, the flexible longitudinal member is deployed such that a deployment angle theta of the flexible longitudinal member is at least 10 degrees and/or less than 80 degrees, e.g., between 30 and 60 degrees. Deployment angle theta is defined as the angle between (a) a vector 64 that is tangent to the flexible longitudinal member at an exit point 68 of the flexible longitudinal member, and is directed away from the catheter, and (b) a distally-directed vector 66 that is parallel to the longitudinal axis 70 of the catheter at exit point 68. (Exit point 68 is identical to one of openings 26a and 26b.) As described hereinabove, the flexible longitudinal member is deployed by passing the flexible longitudinal member through openings 26a and 26b.

Figure 1B:
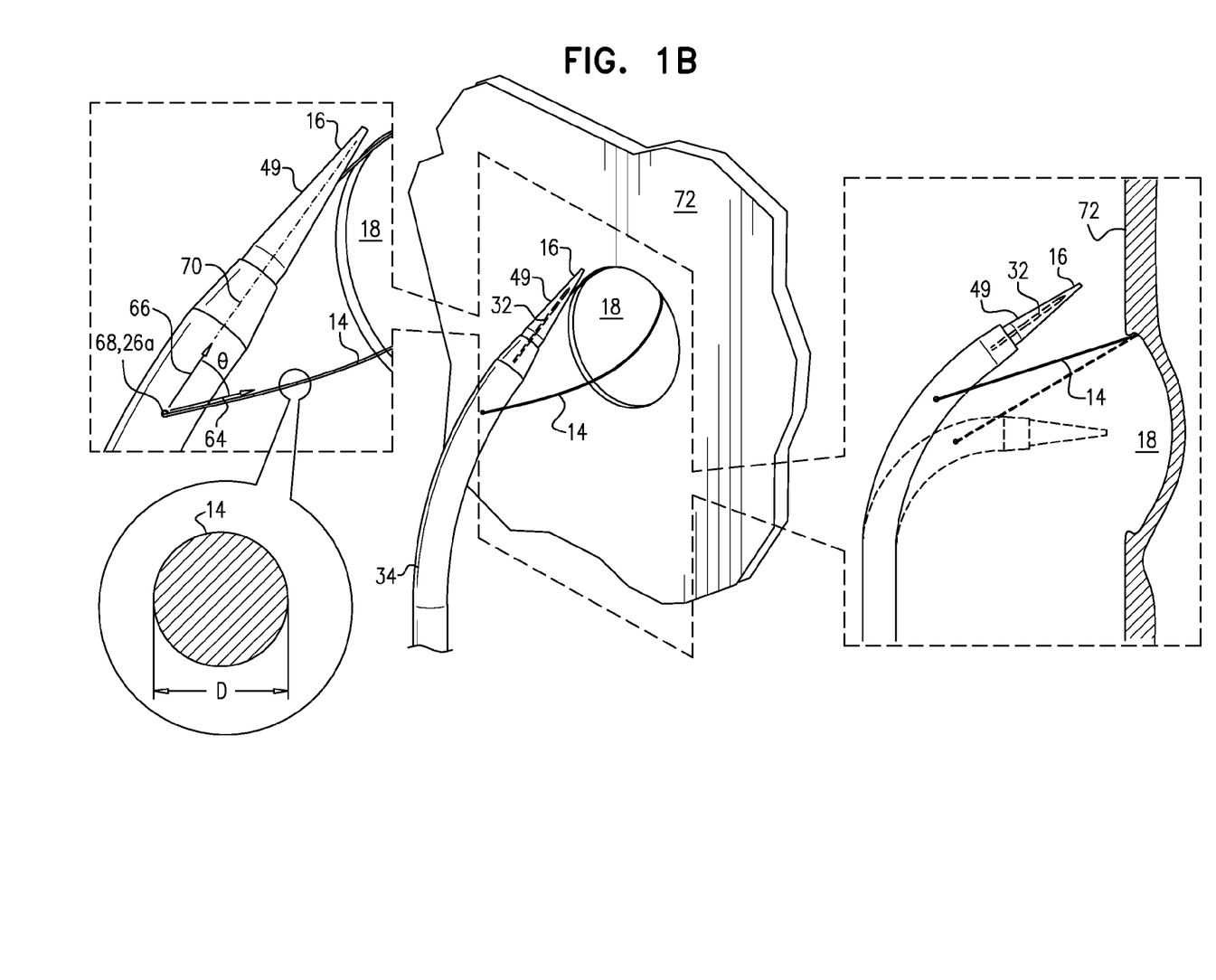
Figure 1C:
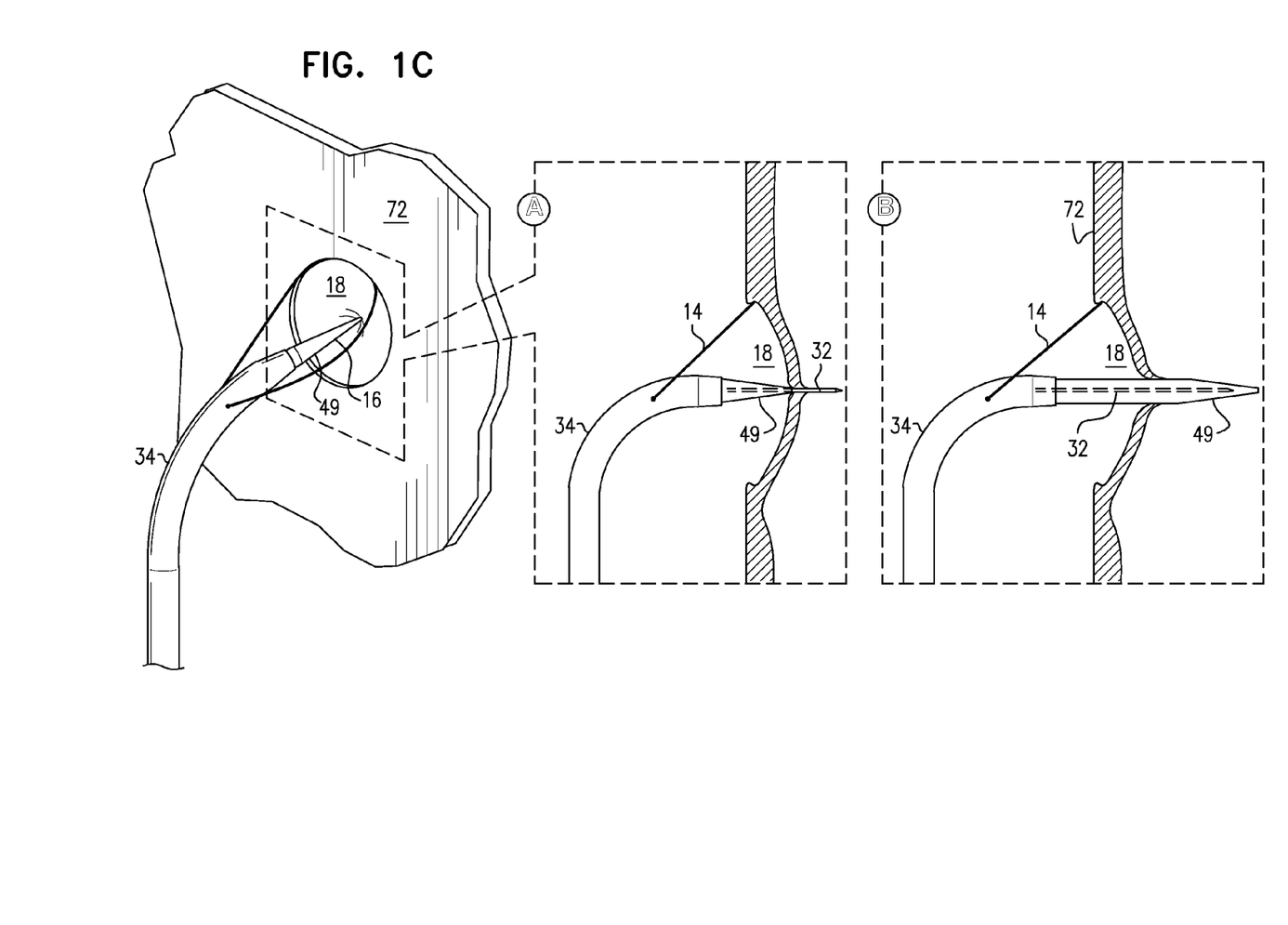

The catheter is steered until fossa ovalis 18 (e.g., an inner perimeter of the fossa ovalis) is contacted with the deployed portion of the flexible longitudinal member, as shown in FIG. 1B. Following the contacting, needle 32 is deployed, typically while within dilator element 49, as shown in the figure. Further typically, as shown in FIG. 1C, dilator tip 16 is brought into contact with the fossa ovalis. The needle is then advanced through a distal opening of the dilator tip and through the fossa ovalis, thus puncturing a hole in the fossa ovalis. Dilator tip 16 then dilates an opening created by the needle.

Figure 1D:
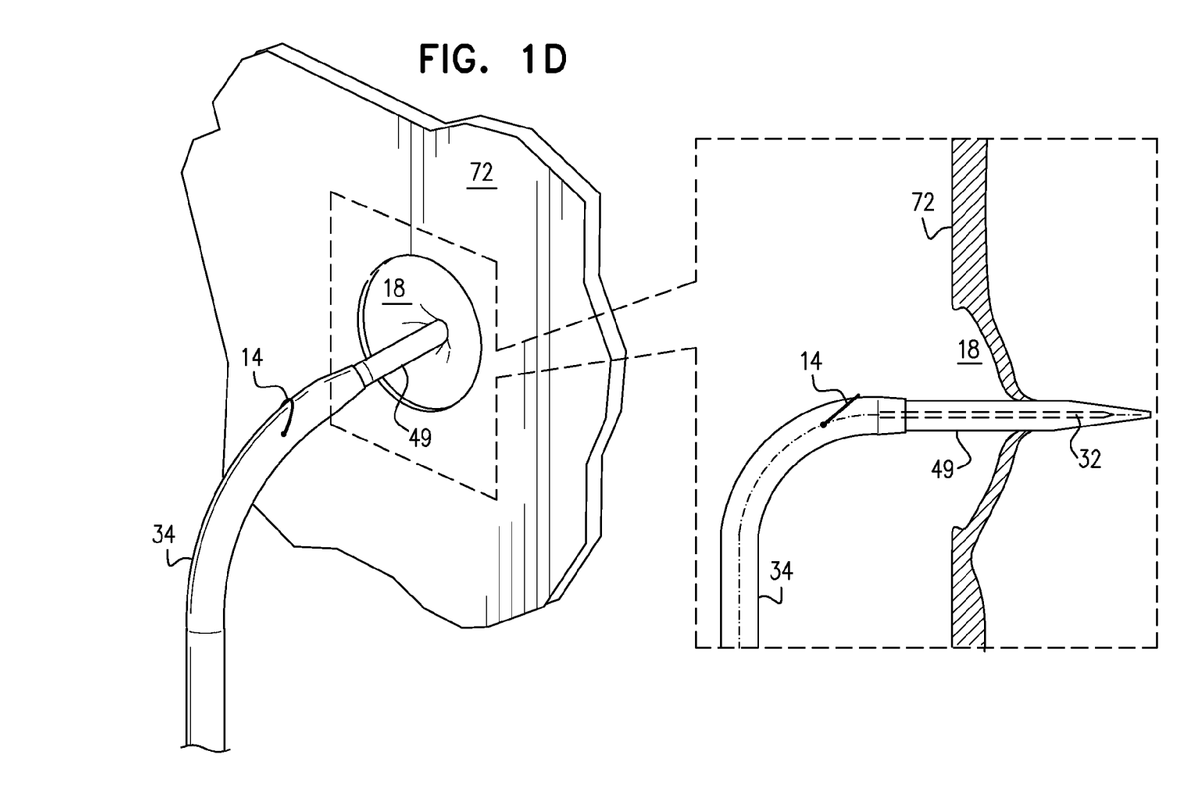

As shown in FIG. 1B, prior to puncturing the fossa ovalis, the distal end of needle 32 is typically passed through the deployed portion of the flexible longitudinal member to a second side of the deployed portion of the flexible longitudinal member that is opposite the first side. (The distal end of the needle is typically passed through the loop while disposed inside of the dilator element.) Subsequently, while the distal end of the needle is on the second side of the deployed portion of the flexible longitudinal member, the deployed portion of the flexible longitudinal member is withdrawn toward the catheter (FIG. 1D).

Typically, catheter 38 is flexibly and/or rotatably steerable via control wires 80 running through control-wire channels 20. The steerability of catheter 38 facilitates better localization of the desired puncturing point.

Figures 3, 4:
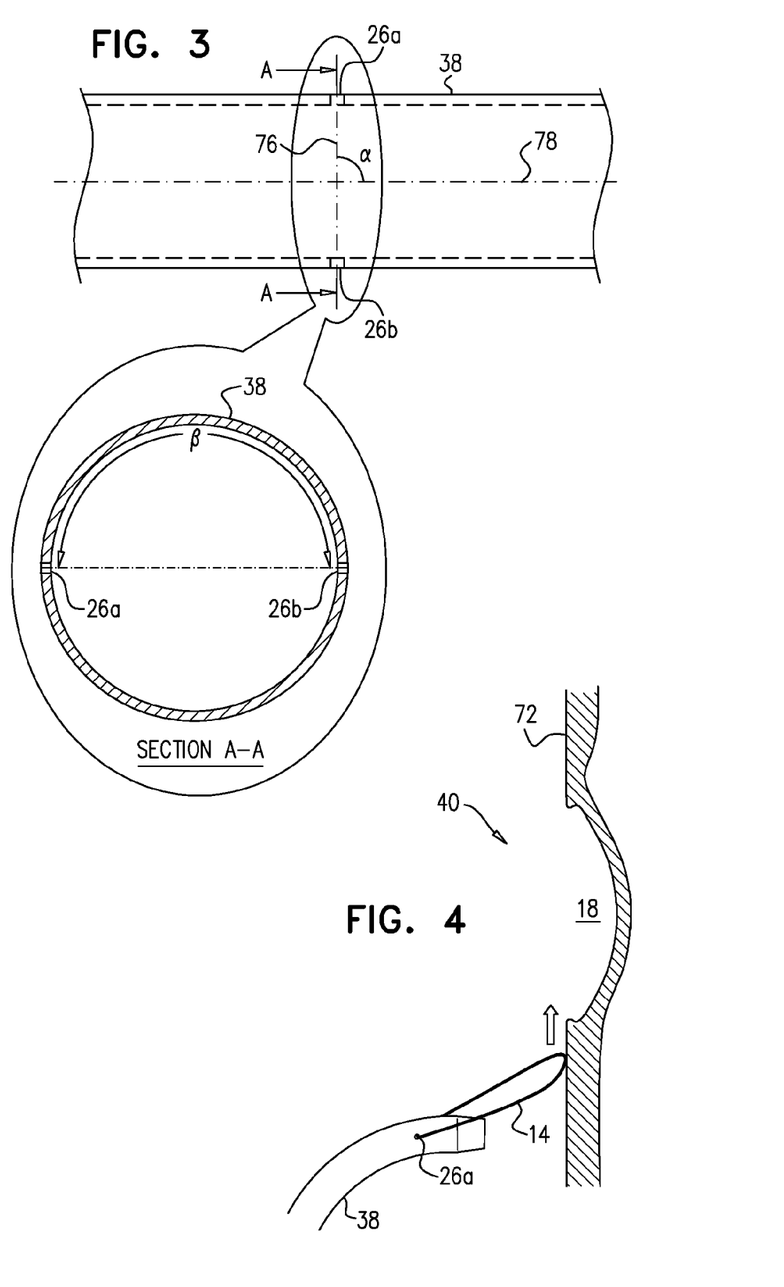
FIG. 3 is a schematic illustration of a catheter, in accordance with some applications of the present invention.
FIG. 4 is a schematic illustration of a method for puncturing the fossa ovalis, in accordance with some applications of the present invention.

Reference is now made to FIG. 3, which is a schematic illustration of catheter 38, in accordance with some applications of the present invention. Typically, first and second openings 26a and 26b are disposed at substantially the same distance from the distal end of the catheter. An advantage of this disposition is that the loop may be deployed in a forward-facing direction, rather than laterally. For example, an angle alpha between (a) a first line 76 running between the first and second lateral openings, and (b) a second line 78 that is parallel to a central longitudinal axis of the catheter when the catheter is straight, may be at least 30 and/or less than 150 degrees, e.g., between 60 and 120 degrees, e.g., between 80 and 100 degrees. (An angle alpha of 90 degrees implies that the first and second openings are disposed at the same distance from the distal end of the catheter.) Alternatively or additionally, the distance of one opening from the distal end of the catheter differs by less than 1 cm from the distance of the other opening.

Further typically, the first and second openings are separated from one another by an angle beta of at least 170 degrees and/or less than 190 degrees (e.g., 180 degrees) measured along a circumference of the catheter. Thus, when the flexible longitudinal member is in its withdrawn position, it "occupies" only 170-190 degrees around the outside surface of the catheter, both prior to deployment and following withdrawal. In contrast, if beta were farther away from 180 degrees, the withdrawn flexible longitudinal member might occupy a relatively large angle, either prior to deployment or following withdrawal. For example, if beta were 90 degrees, the flexible longitudinal member would typically occupy 270 degrees either prior to deployment or following withdrawal, if, as described hereinabove with reference to FIG. 1D, the deployment and withdrawal of the flexible longitudinal member are done from/toward opposite sides of the catheter. It is typically preferred that such a large portion of the flexible longitudinal member not be disposed outside of the catheter when the flexible longitudinal member is in its withdrawn position, since the risk of collateral damage to tissue typically increases as more of the flexible longitudinal member is exposed. The angle beta of 170-190 degrees is thus advantageous, particularly when the deployment and withdrawal are done from/to opposite sides of the catheter. (It is noted that for some procedures or for some patients, an angle beta outside of 170-190 degrees is appropriate.)

Reference is now made to FIG. 4, which is a schematic illustration of a method 40 for puncturing the fossa ovalis, in accordance with some applications of the present invention. Before contacting the fossa ovalis with the deployed portion of flexible longitudinal member 14, the deployed portion of the flexible longitudinal member is moved along a surface of interatrial septum 72, until the flexible longitudinal member contacts the fossa ovalis. In some applications, as shown in FIG. 4, the deployed portion of the flexible longitudinal member is moved toward the fossa ovalis from below the fossa ovalis. In some applications, the flexible longitudinal member is radiopaque and/or is coupled to a plurality of radiopaque markers. In such applications, fluoroscopic imaging is used to view the flexible longitudinal member during and after deployment thereof. For example, fluoroscopic imaging may be used to view the flexible longitudinal member as it is moved toward the fossa ovalis, in order to help identify when the flexible longitudinal member has reached the fossa ovalis.

Figure 5:
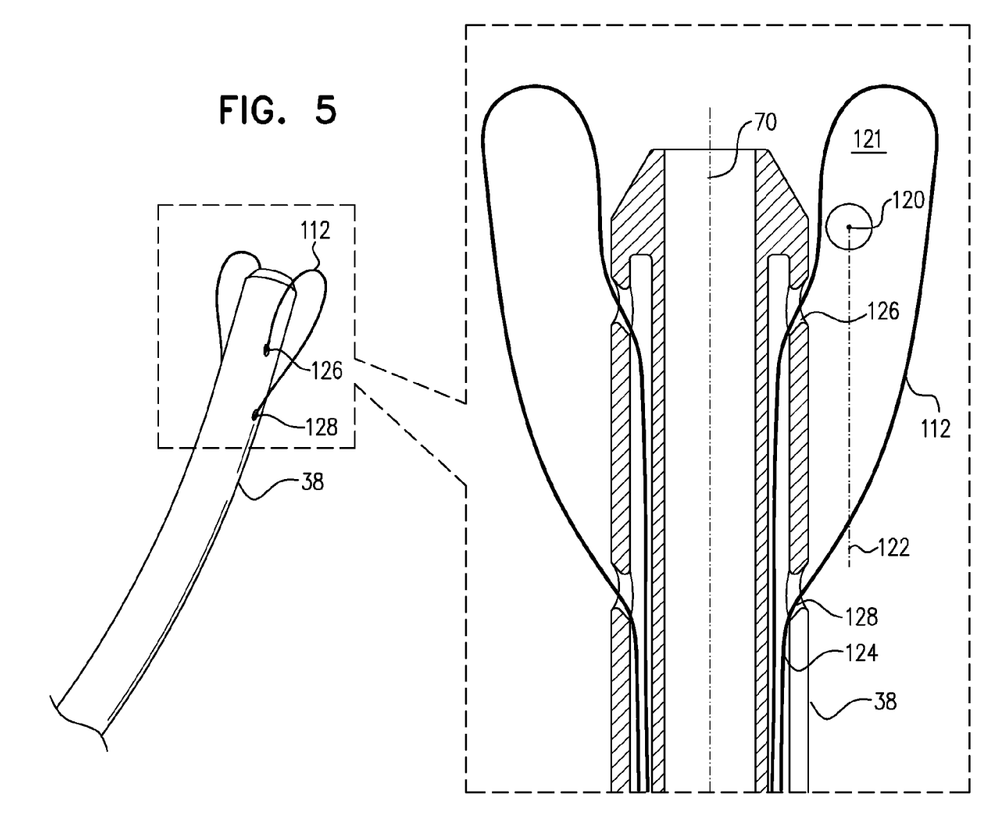
FIG. 5 is a schematic illustration of apparatus used for finding and/or measuring an opening of an appendage of an atrium, in accordance with some applications of the present invention.

Reference is now made to FIG. 5, which is a schematic illustration of apparatus used for finding and/or measuring an opening of an appendage of an atrium (e.g., a left atrium) of a subject, in accordance with some applications of the present invention. FIG. 5 shows a cross-section of catheter 38. One or more loops 112 are deployable from a wall (e.g., a lateral wall) of catheter 38. As described hereinbelow, loops 112 are appendage-finding and/or appendage-measuring loops, in that they may be used to find and/or measure the appendage of the atrium. In some applications, when finding and/or measuring the opening of the appendage, exactly one loop is deployed. In other applications, two or more loops are deployed.

To facilitate the finding and/or measuring of the opening, each loop 112 is deployed such that the distal end thereof is distal to the distal end of the catheter. Furthermore, each loop is deployed such that a normal 120 to a plane 121 defined by the loop intersects a line 122 that is parallel to longitudinal axis 70 of the catheter at an angle that is at least 10 and/or less than 90 degrees. For example, the cross-section of FIG. 5 shows the loops "in plane," such that normal 120 runs into the page, and the angle between the normal and line 122 is 90 degrees. In some applications, as shown in FIG. 5, each loop includes a longitudinal member 124 that passes through a first opening 126 and a second opening 128 in the catheter wall. In such applications, the loop is deployed by passing longitudinal member 124 through at least one of the first and second openings.

Figure 6A:
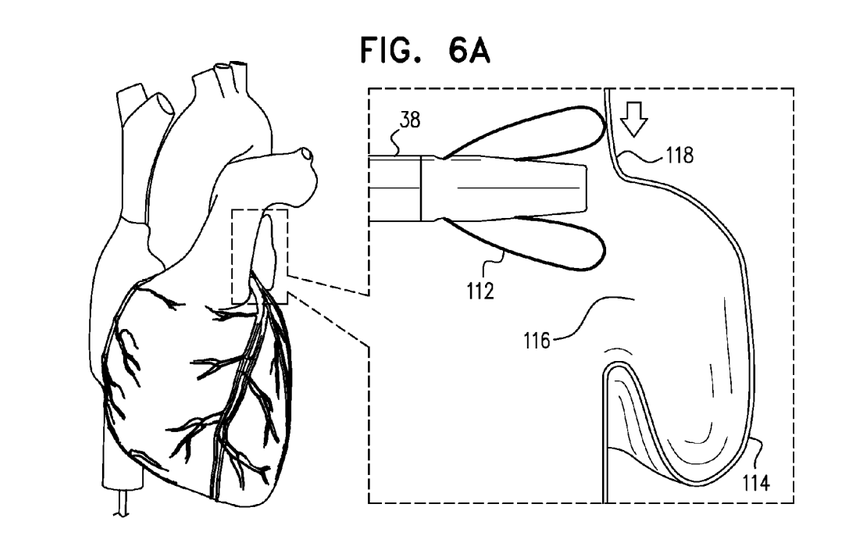
FIGS. 6A-E are schematic illustrations of a method for finding and/or measuring an opening of an appendage of an atrium, in accordance with some applications of the present invention.

Reference is now made to FIGS. 6A-D, which are schematic illustrations of a method for finding and/or measuring an opening 116 of an appendage (e.g., an LAA) 114, in accordance with some applications of the present invention. FIG. 6A shows loops 112 being used to find opening 116. A distal end of at least one of the loops is moved along the wall 118 of the atrium, typically while being imaged. (For example, the loop may be radiopaque, and fluoroscopic imaging may be used to view the loop.) Upon reaching the opening, the loop loses contact with wall 118, and/or moves (e.g., "lunges" forward) into appendage 114. The loss of contact with the wall, and/or the moving into the appendage, may be observed via imaging, and/or may be otherwise sensed by the user of the apparatus. (For example, a sudden "jerk" may indicate that the loop has moved into the appendage.) In response to the distal end of the loop reaching the opening, the opening is identified.

Figure 6B:
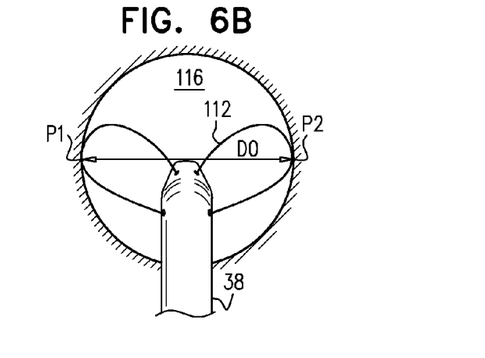

FIGS. 6B-E show the measuring of the opening, following the identification thereof. In FIG. 6B, loops 112 are expanded until they contact at least two points P1 and P2 on a perimeter of the opening. Then, the distance D0 between the points is measured, by using imaging to view the loops while they are in contact with the points. (For example, as described above, the loop(s) may be radiopaque, and fluoroscopic imaging may be used.) In some applications, alternatively or additionally to using imaging, D0 is measured by utilizing markers on proximal portions of the loops (i.e., on proximal portions of longitudinal members 124) that indicate the extent to which the loops have been expanded. In some applications, multiple measurements of D0 are taken for respective multiple contact points, and the diameter of the opening is ascertained from the multiple measurements.

Figure 6C:
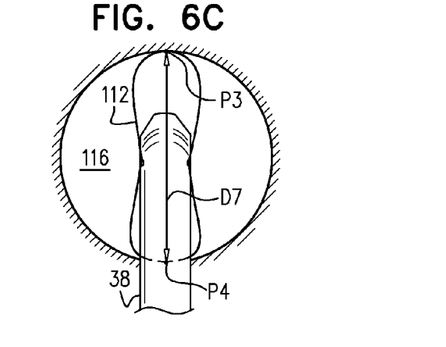

In some applications, as shown in FIG. 6C, a distance D7 that is perpendicular to D0 is measured, alternatively or additionally to measuring D0. An advantage of measuring D7 in addition to D0 is that both the "width" and the "height" of the opening may be measured, such that a more precise assessment of the size of the opening may be made, relative to if only a single distance were measured. In addition, both distances together give some indication as to the shape of the opening; for example, it may be ascertained that the opening is slightly elliptical. In some applications, D7 is measured by deploying loops that expand as shown in FIG. 6C, until the loops contact a second pair of points P3 and P4 on the perimeter of the opening. In other applications, the catheter is rotated about its longitudinal axis by approximately 90 degrees, relative to its orientation in FIG. 6B, and the loops are adjusted until they contact points P3 and P4.

Figure 6D:
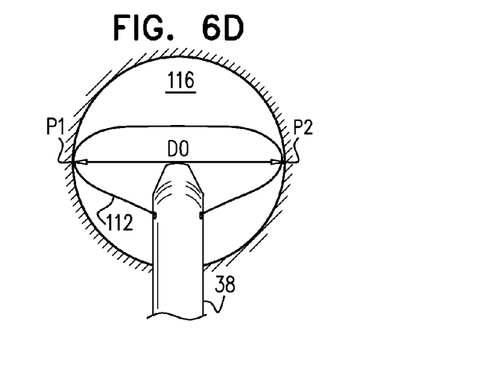
Figure 6E:
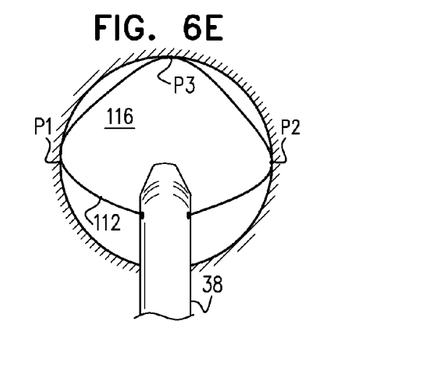

FIGS. 6D-E show applications in which a single loop is deployed. The single loop may be used to measure D0 or D7, as shown in FIG. 6D. Alternatively or additionally, the loop can be used to measure the approximate half-circumference of the opening, as shown in FIG. 6E, by contacting at least three points distributed along the half-circumference of the opening, and summing the distances between successive pairs of points.

In some applications, at least one of loops 112 is also a fossa-ovalis-finding loop, i.e., at least one of the loops is used both for finding the fossa ovalis and, following the puncture of the fossa ovalis and insertion of the catheter into the left atrium, for finding and/or measuring the LAA. In such applications, longitudinal member 124 may be identical to the longitudinal member described hereinabove with reference to FIGS. 1A-D. In other applications, a first loop is used to find the fossa ovalis, and a second, different loop is used to find and/or measure the LAA.

In some applications, the measurement of the opening is used to select an implant of an appropriate size. The implant is then passed through the catheter, delivered to the opening, and implanted in the opening. For example, some subjects are in need of an LAA-closure implant, i.e., an implant that fills the LAA opening and generally isolates the LAA from the rest of the left atrium. Without prior measurement of the LAA opening, it is possible that an inappropriately-sized implant, which does not properly close the LAA, may be implanted. Hence, the measurement of the opening, as described hereinabove, facilitates the selection of an appropriately-sized implant. Furthermore, the measurement apparatus also functions as a delivery apparatus, such that the measurement and the delivery may be performed during the same procedure, with only a single insertion of the catheter into the atrium.

Figure 7:
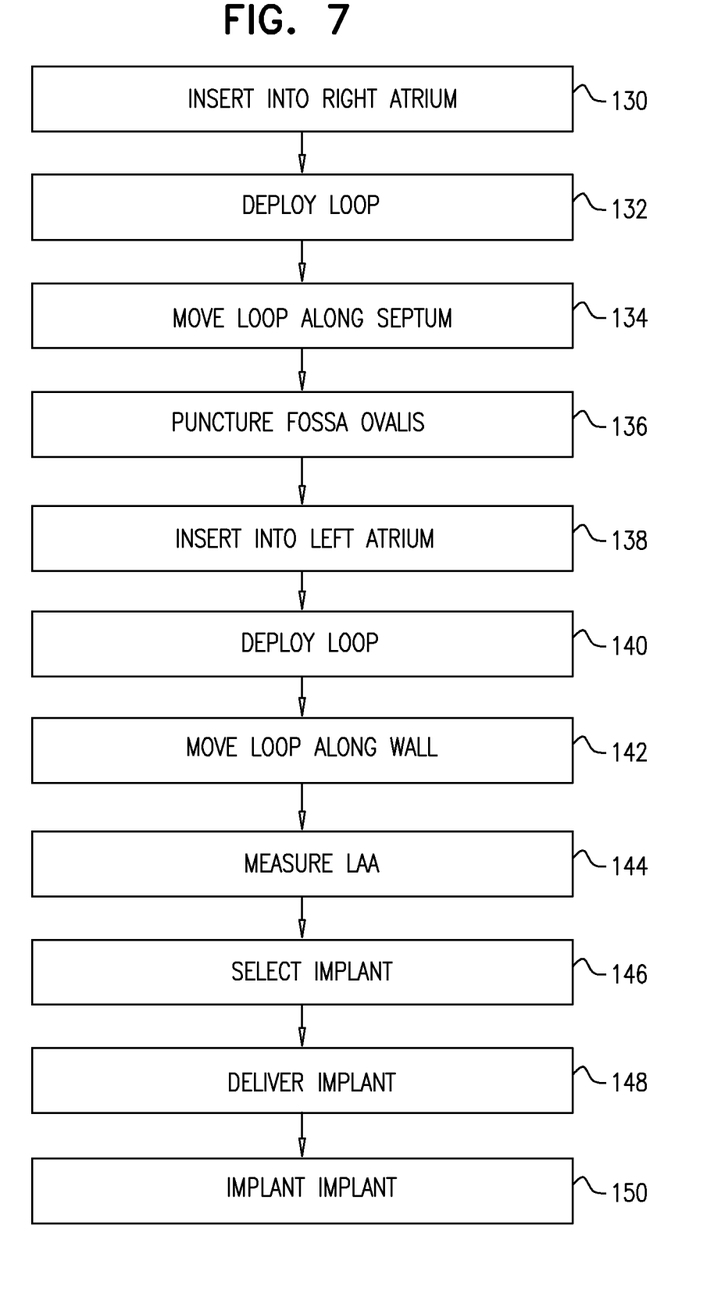
FIG. 7 is a flowchart for a method for implanting an implant in an LAA of a subject, in accordance with some applications of the present invention.

Reference is now made to FIG. 7, which is a flowchart for a method for implanting an implant in an LAA of a subject, in accordance with some applications of the present invention. First, at a first insertion step 130, the catheter is inserted into the right atrium. Then, at a first deployment step 132, at least one fossa-ovalis-finding loop is deployed from the wall of the catheter, e.g., as described hereinabove with reference to FIG. 1B. At a first moving step 134, the fossa-ovalis-finding loop is moved along the interatrial septum, until the fossa-ovalis-finding loop contacts the fossa ovalis, as shown in FIG. 1B. Then, at a puncturing step 136, the fossa ovalis is punctured by passing a puncturing element out of the distal end of the catheter, e.g., as described hereinabove with reference to FIG. 1C. The catheter is then inserted into the left atrium at a second insertion step 138, and, at a second deployment step 140, at least one appendage-finding loop is deployed. (As described hereinabove, the fossa-ovalis-finding loop may also serve as an appendage-finding loop.) At a second moving step 142, the appendage-finding loop is moved along the arterial wall, as described hereinabove with reference to FIG. 6A. Following the identification of the LAA, the LAA is measured at a measuring step 144, as described hereinabove with reference to FIGS. 6B-D. In response to the measuring, an appropriately-sized implant is selected, at an implant-selection step 146. Finally, the implant is delivered to the LAA at a delivery step 148, and is implanted in the opening of the LAA at an implanting step 150.

In general, apparatus described herein may be used, and techniques described herein may be practiced, in combination with apparatus and techniques described in (i) U.S. patent application Ser. No. 14/245,135 to Maisano et al., published as US 2014/0309675, (ii) PCT/IL2014/050338 to Maisano et al., published as WO 2014/170890, and (iii) U.S. patent application Ser. No. 14/513,435 to Sapir et al., published as US 2016/0100859, each of which is entitled "Fossa Ovalis Penetration" and is incorporated herein by reference.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for measuring an opening of an appendage of an atrium of a subject, the method comprising:
   inserting a catheter into the atrium of the subject;
   deploying at least one loop from a lateral wall of the catheter, such that a distal end of the loop is distal to a distal end of the catheter; and
   using the loop to measure the opening of the appendage, wherein measuring the opening comprises:
      expanding the loop until the loop contacts at least two points on a perimeter of the opening; and
      measuring a distance between the points, by using imaging to view the loop while it is in contact with the points.

2. The method according to claim 1, wherein the method comprises measuring an opening of an appendage of a left atrium of the subject.

3. The method according to claim 1, wherein deploying the loop comprises deploying the loop such that a normal to a plane defined by the loop intersects a line that is parallel to a longitudinal axis of the catheter at an angle that is between 10 and 90 degrees.

4. The method according to claim 1, wherein the method further comprises, before measuring the opening:
   moving the distal end of the loop along a wall of the atrium; and
   identifying the opening in response to the distal end of the loop reaching the opening.

5. The method according to claim 1, further comprising:
   in response to the measuring, selecting an implant of an appropriate size;
   delivering the implant to the opening, by passing the implant through the catheter; and
   implanting the implant in the opening.

6. The method according to claim 1,
   wherein the loop includes a longitudinal member that passes through a first opening and a second opening in the catheter wall, and
   wherein deploying the loop comprises deploying the loop by passing the longitudinal member through at least one of the first and second openings.

7. The method according to claim 1, wherein deploying the at least one loop comprises deploying at least two loops.

8. The method according to claim 7, wherein deploying the at least two loops comprises deploying more than two loops.

9. A method for measuring an opening of an appendage of an atrium of a subject, the method comprising:
   inserting a catheter into the atrium of the subject;
   deploying at least one loop from a lateral wall of the catheter, such that a distal end of the loop is distal to a distal end of the catheter; and
   using the loop to measure the opening of the appendage, wherein measuring the opening comprises:
      expanding the loop until the loop contacts at least two points on a perimeter of the opening; and
      measuring a distance between the points, by utilizing a marker on a proximal portion of the loop that indicates an extent to which the loop has been expanded.

10. The method according to claim 8,
    wherein measuring the distance between the points further comprises using imaging to view the loop while it is in contact with the points.

11. The method according to claim 9, wherein the method further comprises, before measuring the opening:
    moving the distal end of the loop along a wall of the atrium; and
    identifying the opening in response to the distal end of the loop reaching the opening.

12. A method for measuring an opening of an appendage of an atrium of a subject, the method comprising:
    inserting a catheter into the atrium of the subject;
    deploying at least one loop from a lateral wall of the catheter, such that a distal end of the loop is distal to a distal end of the catheter; and
    using the loop to measure the opening of the appendage,
    wherein the atrium is a left atrium,
    wherein the loop is an appendage-finding and fossa-ovalis-finding loop, and
    wherein the method further comprises, prior to inserting the catheter into the left atrium:
       inserting the catheter into a right atrium of the subject;
       deploying at least the loop from the lateral wall of the catheter;

moving the loop along an interatrial septum of the subject, until the loop contacts a fossa ovalis of the subject; and in response to the loop contacting the fossa ovalis, puncturing the fossa ovalis by passing a puncturing element out of the distal end of the catheter.

13. The method according to claim 12, wherein the method further comprises, before measuring the opening:
moving the distal end of the loop along a wall of the atrium; and
identifying the opening in response to the distal end of the loop reaching the opening.

14. A method for measuring an opening of an appendage of a left atrium of a subject, the method comprising:
inserting a catheter into the atrium of the subject;
deploying at least one appendage-finding loop from a lateral wall of the catheter, such that a distal end of the loop is distal to a distal end of the catheter; and
using the appendage-finding loop to measure the opening of the appendage,
wherein the method further comprises, prior to inserting the catheter into the left atrium:
inserting the catheter into a right atrium of the subject;
deploying at least one fossa-ovalis-finding loop, which is different from the appendage-finding loop, from the lateral wall of the catheter;
moving the fossa-ovalis-finding loop along an interatrial septum of the subject, until the fossa-ovalis-finding loop contacts a fossa ovalis of the subject; and
in response to the fossa-ovalis-finding loop contacting the fossa ovalis, puncturing the fossa ovalis by passing a puncturing element out of the distal end of the catheter.

15. The method according to claim 14, wherein the method further comprises, before measuring the opening:
moving the distal end of the loop along a wall of the atrium; and
identifying the opening in response to the distal end of the loop reaching the opening.

16. A method for measuring an opening of an appendage of an atrium of a subject, the method comprising:
inserting a catheter into the atrium of the subject;
deploying at least one loop from a lateral wall of the catheter, such that a distal end of the loop is distal to a distal end of the catheter; and
using the loop to measure the opening of the appendage,
wherein measuring the opening of the appendage comprises measuring (a) a distance between a first pair of points on a perimeter of the opening, and (b) a distance between a second pair of points on the perimeter of the opening.

17. The method according to claim 16, wherein the method further comprises, before measuring the opening:
moving the distal end of the loop along a wall of the atrium; and
identifying the opening in response to the distal end of the loop reaching the opening.

* * * * *